United States Patent [19]

Rooney et al.

[11] 3,995,039

[45] Nov. 30, 1976

[54] PYRAZOLO [1,5-a] [1,3,5] TRIAZINES

[75] Inventors: Clarence Stanley Rooney, Beaconsfield; Haydn Windsor Richard Williams, Dollard des Ormeaux, both of Canada

[73] Assignee: Merck & Co., Inc., Rahway, N.J.

[22] Filed: May 27, 1975

[21] Appl. No.: 581,388

[52] U.S. Cl. .......................... 424/249; 260/249.5
[51] Int. Cl.² ............... C07D 251/72; A61K 31/395
[58] Field of Search .................. 260/249.5; 424/249

[56] References Cited
UNITED STATES PATENTS 3,910,907  10/1975  O'Brien et al. .................. 260/249.5

*Primary Examiner*—John M. Ford
*Attorney, Agent, or Firm*—Edmunde D. Riedl; David L. Rose; J. Jerome Behan

[57] ABSTRACT

Novel pyrazolo [1,5-a] [1,3,5] triazines are provided which are active agents to inhibit bronchial constriction with very low chronotropic effects. The novel compounds are prepared by the reaction of an appropiately substituted 1-amidino-5-amino pyrazole with an appropriately substituted trialkyl orthoester. Suitable compositions for utilizing this bronchodilating activity by administration to humans are also disclosed.

13 Claims, No Drawings

PYRAZOLO [1,5-A] [1,3,5] TRIAZINES

SUMMARY OF THE INVENTION

This invention concerns novel pyrazolo [1,5-a] [1,3,5] triazines which are active bronchodilating agents. Thus, it is an object of this invention to provide for such novel compounds. Another object is to provide for processes for the preparation of such compounds. A still further object is to provide for compositions containing said compounds as the active ingredient for administration to humans for the relief of bronchial constriction.

DESCRIPTION OF THE INVENTION

This invention is concerned with novel pyrazolo-[1,5-a] [1,3,5] triazine compounds that effectively inhibit bronchial constriction induced by histamine or other bronchial constricting substances. The pyrazolotriazine compounds of this invention have been found to be superior to most known bronchodilating agents because they are orally active and produce relatively low chronotropic effects. Additionally, some of the compounds exhibit useful hypotensive properties.

The novel pyrazolotriazine compounds of this invention have the structure:

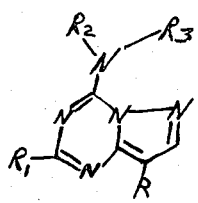

and pharmacologically acceptable acid addition salts thereof wherein R is a heterocyclic substituent attached through one of its carbon atoms to the pyrazolotriazine moiety preferably an N-containing heterocyclic group selected from pyridyl, pyrimidinyl or pyrazinyl; $R_1$ represents hydrogen or loweralkyl, advantageously, having from one to five carbons; $R_2$ represents hydrogen or loweralkyl; and $R_3$ represents hydrogen, loweralkyl, loweralkanoyl, carbamoyl or N-loweralkylcarbamoyl.

The preferred compounds included within the above structural formula are those wherein R is pyridyl, pyrimidinyl or pyrazinyl; $R_1$ is hydrogen; $R_2$ is hydrogen or methyl; and $R_3$ is hydrogen, methyl, acetyl or N-ethyl carbamoyl. A still further preferred group compounds of the above structural formula is realized when R is pyridyl; $R_1$ is hydrogen; and $R_2$ and $R_3$ are hydrogen.

The term "loweralkyl" when employed in the instant specification and claims, is intended to include those alkyl groups containing from 1 to 5 carbon atoms in either a straight or branced chain such as methyl, ethyl, propyl, isopropyl, butyl, tbutyl, amyl, and the like.

The term "loweralkanoyl" includes those alkanoyl groups of from 2 to 5 carbon atoms such as acetyl, propionyl, butyryl, and the like.

The pharmacologically acceptable acid addition salts include those salts prepared from mineral acids such as hydrohalic, nitric, sulfuric, phosphoric, and the like; and also organic acids such as acetic, citric, pivalic, and the like. Any non-toxic acid which forms a salt with the instant compounds is suitable for the instant invention.

The pyrazolotriazine compounds can be prepared by the reaction of a 1-amidino-4-R-5-aminopyrazole with a trialkyl orthoester of the formula: $R_1C(O alk)_3$ wherein $R_1$ is hydrogen or loweralkyl and alk is a loweralkyl to provide product I wherein $R^1$ is hydrogen or loweralkyl and $R^2$ is amino. These reactions are carried out by heating the reactants at from room temperature to 100° C. for from ½ to 6 hours with or without the presence of a solvent. When employed, suitable solvents are xylene, diethyleneglycol- dimethyl ether, and the like. The ureido or amino group can be converted to an acylamino, mono- or di-alkylamino groups. This is accomplished by acylating the amino group with acylating reagents, preparing the ureido group with reagents such as loweralkylisocyanates, and alkylating the amino group using alkylating agents such as alkylhalides, and the like. The mono- and di-alkylamino derivatives are also obtained when the appropriate N-alkyl or N,N-dialkylamidino 4-R-5-amino-pyrazole is used as the starting material.

The 1-amidino-4-R-5-aminopyrazole starting substance can be made by heating a solution of R-malondialdehyde and hydroxylamine hydrohalide. The 4-R-isoxazole formed need not be isolated and purified before being treated with a strong base, such as an alkali metal hydroxide to convert it to 2-formyl-2-R-acetonitrile. Heating a suspension or solution of this compounds with aminoguanidine or $N_4$-mono or dialkylaminoguanidine provides a good yield of 1-amidino-4-R-5-aminopyrazoles.

The pyrazolotriazine compounds can be administered in formulations suitable for oral or parenteral administration or in aerosol preparations. The formulations are prepared by conventional methods with pharmaceutical carriers and may, if desired, be combined with other desired pharmacologically active compounds. For example, a capsule can be prepared by known methods employing lactose as an excipient and containing per unit dosage 5–25mgs. of active compound. Unit dosages can range between about 5–100 mgs. for administration as prescribed by the physician.

The following examples describe the preparation of certain representative pyrazolotriazine compounds that have been found to be effective bronchodilating agents.

EXAMPLE 1

4-Amino-8-(4-pyridyl)-pyrazolo[1,5-a] [1,3,5] triazine

A. Preparation of 2-Formyl-2-(4-pyridyl)acetonitrile

4-Pyridine malondialdehyde (29.8 g., 0.2 mole) is added to a solution of hydroxylamine hydrochloride (16.0 g., 0.23 moles) in water (500 ml.) and the mixture is heated at 65°–70° C. for two hours. When cool, the solution is made basic with 10% sodium carbonate solution and the crude 4-(4-pyridyl)isoxazole is filtered off, washed with water and drained on filter. The solid is suspended in water (500 ml.) and made basic with 5N sodium hydroxide (50 ml.). The suspension is heated briefly until solution occurs, then cooled to ambient temperature and acidified with citric acid yielding 25.4 g. (86%) of 2-formyl-2-(4-pyridyl) acetonitrile as a pale pinkish powder.

B. Preparation of 1-Amidino-4-(4-pyridyl)-5-aminopyrazole

To 2-formyl-2-(4-pyridyl)-acetonitrile (7.3 g., 50 mmoles) suspended in 1N hydrochloric acid (100 ml.) is added in small portions aminoguanidine bicarbonate (6.8 g., 50 mmoles) and the mixture is heated on a steam bath for one hour. After a further three hours at room temperature, the mixture is filtered and the filtrate made basic with 2N sodium hydroxide solution yielding 4.0 g. (40%) of 1-amidino-4-(4-pyridyl)-5-aminopyrazole, m.p. 179°–181° C. Recrystallization from ethyl acetate gives product melting at 185°–186° C.

Analysis calculated for $C_9H_{10}N_6$: C, 53.45; H, 4.98; N, 41.56; Found: C, 53.26; H, 5.09; N, 41.81.

C. Preparation of 4-Amino-8-(4-pyridyl)-pyrazolo[1,5-a]-[1,3,5]triazine

1-Amidino-4-(4-pyridyl)-5-aminopyrazole (1.616 g., 8 mmoles) is suspended in triethyl orthoformate (20 ml.) and the mixture is heated under reflux for two hours. When cool, the crude product is collected and recrystallized from boiling dimethylformamide (30 ml.) giving 957 mg. of 4-amino-8-(4-pyridyl)-pyrazolo[1,5-a][1,3,5]triazine, m.p. 330–333° C. (dec.). Addition of 95% ethanol to the mother liquors gives a further 182 mg. of product, total yield 67%.

Analysis calculated for $C_{10}H_8N_6$: C, 56.59; H, 3.80; N, 39.61; Found: C, 55.55; H, 4.12; N, 39.78.

EXAMPLE 2

4-Amino-8-(4-pyrimidinyl)-pyrazolo[1,5-a][1,3,5]triazine

A. By replacing the 4-pyridine malondialdehyde employed in Example 1A by an equivalent quantity of 4-pyrimidine malondialdehyde there is obtained 2-formyl-2-(4-pyrimidinyl)acetonitrile in almost quantitative yield. The compound following sublimation at 160° C. at 0.005 mm. has m.p. 262–265° C.

Analysis calculated for $C_7H_5N_3O$: C, 57.14; H, 3.43; N, 28.56; Found: C, 57.29; H, 3.68; N, 28.70.

This compound is converted to 1-amidino-4-(4-pyrimidinyl)-5-aminopyrazole by the procedure described in Example 1B in a 51% yield. The compound crystallizes from methanol in colorless glistening plates, m.p. 184°–184.5° C. (dec.). Molecular weight by mass spectrum is 203.

C. By replacing the 1-amidino-4-(4-pyridyl)-5-aminopyrazole in Example 1C with an equivalent quantity of 1-amidino-4-(4-pyrimidinyl)-5-aminopyrazole there is obtained an 80% yield of 4-amino-8-(4-pyrimidinyl)-pyrazolo-[1,5-a][1,3,5]triazine which separates from boiling dimethylformamide in crystals melting at about 340° C. (dec.).

Analysis calculated for $C_9H_7N_4$: C, 50.70; H, 3.31; N, 45.99; Found: C, 51.34; H, 3.49; N, 45.27.

EXAMPLE 3

4-Amino-8-(2-pyrazinyl)-pyrazolo[1,5-a][1,3,5]triazine

A. Preparation of 2-Formyl-2-(2-pyrazinyl)acetonitrile 4-(2-Pyrazinyl)-isoxazole (5.40 g., 36.7 mmoles) is suspended in water (50 ml.) and 5N sodium hydroxide is added. The mixture is warmed until a clear solution is obtained, then cooled and acidified with acetic acid giving 3.5 g. (65%) yield of 2-formyl-2-(2-pyrazinyl)-acetonitrile, m.p. 192°–194° C.

Analysis calculated for $C_7H_5N_3O$: C, 57.14; H, 3.42; N, 28.56; Found: C, 57.11; H, 3.45; N, 28.71.

B. Preparation of 1-Amidino-4-(2-pyrazinyl)-5-aminopyrazole

By replacing the 2-formyl-2-(4-pyridyl)-acetonitrile employed in Example 1B with an equivalent quantity of 2-formyl-2-(2-pyrazinyl)acetonitrile, there is obtained 1-amidino-4-(2-pyrazinyl)-5-aminopyrazole in 45% yield. Following crystallization from 95% ethanol the product melts at 185.5°–187° C.

Analysis calculated for $C_8H_9N_7$: C, 47.28; H, 4.46; N, 48.25; Found: C, 46.88; H, 4.49; N, 48.29.

C. Preparation of 4-Amino-8-(2-pyrazinyl)-pyrazolo[1,5-a][1,3,5]triazine

By replacing the 1-amidino-4-(4-pyridyl)-5-aminopyrazole employed in Example 1C with an equivalent quantity of 1-amidino-4-(2-pyrazinyl)-5-aminopyrazole and following substantially the same procedure described in Example 1C there is obtained a 75% yield of 4-amino-8-(2-pyrazinyl)-pyrazolo[1,5-a][1,3,5]triazine. The product separates from boiling dimethylformamide in crystals melting above 360° C.

Analysis calculated for $C_9H_7N_7$: C, 50.70; H, 3.31; N, 45.99; Found: C, 50.77; H, 4.00; N, 45.56.

EXAMPLE 4

4-Acetamido-8-(4-pyridyl)-pyrazolo[1,5-a][1,3,5]triazine

4-Amino-8-(4-pyridyl)-pyrazolo[1,5-a][1,3,5]triazine (2.12 g., 10 mmole) is suspended in acetic anhydride (30 ml.) and anhydrous sodium acetate (1.5 g.) is added. The mixture is heated under reflux for about 50 minutes. On cooling the mixture, the product crystallizes, is collected, slurried cold water (15 ml.) and refiltered yielding 1.7 g. (67%) of 4-acetamido-84-pyridyl)-pyrazolo[1,5-a]-[1,3,5]triazine, m.p. ca. 225° C. (dec.) with vigorous gas evolution. Following recrystallization from methanol the product melts at 229° C. (dec.).

Analysis calculated for $C_{12}H_{10}N_6O$: C, 56.68; H, 4.31; N, 33.06; Found: C, 56.64; H, 3.96; N, 32.85.

By replacing the pyrazolotriazine employed in Example 4 by an equivalent quantity of the end product of Example 2 or Example 3 there is obtained, respectively, 4-acetamido-8-(4-pyrimidinyl)-pyrazolo-[1,5-a][1,3,5]triazine and 4-acetamido-8-(2-pyrazinyl)-pyrazolo[1,5-a][1,3,5]triazine.

EXAMPLE 5

4-($N^2$-ethylureido)-8-(4-pyridyl)-pyrazolo[1,5-a]-[1,3,5]triazine hydrochloride A mixture of 4-amino-8-(4-pyridyl)-pyrazolo-[1,5-a][1,3,5]triazine (4.24 g., 20 mmole), ethyl isocyanate (70 ml.) and triethylamine (7 ml.) is stirred under reflux for 17 hours. The mixture is cooled and the crude product collected and washed with either to afford 3.5 g. (62%) of solid. The solid is converted to 4-($N$-ethylureido)-8-(4-pyridyl)-pyrazolo-[1,5-a][1,3,5]triazine hydrochloride by suspending it in methanol (50 ml.) and adding a slight excess of ethanolic hydrogen chloride solution. The mixture is heated to boiling and the solutions treated with charcoal, filtered and cooled to give 1.45 g. (23) of product m.p. 327°–330° C.

Analysis calculated for $C_{13}H_{13}N_7O$ HCl C, N, 30.66 Found: C, N, 30.35 nmr $b^{D_2O}$ 8.72 (d, 2H, J=7 Hz, pyridyl-H), 8.53 (s, 1H, pyrazolotriazinyl-H), 8.28 (d, 2H, J=7 Hz, pyridyl-H), 8.11 (s, 1H, pyrazolotriazinyl-H), 4.95 HDO, 3.60 (q, 2H, J=7 Hz, $CH_2$), 1.40 (t, 3H, J=7 Hz, $CH_3$).

EXAMPLE 6

1-(N,N-Dimethylamidino)-4-(4-pyridyl)-5-amino-1H-pyrazole Hydrochloride hemihydrate 2-Formyl-2-(4-pyridyl)-acetonitrile (12 g., 85 mmoles) and N,N-dimethylaminoquanidine hydroiodide (19.5 g., 89 mmoles) are added to 1N hydrochloric acid (89 ml.) and the mixture is heated at 80° for 1 hour. After a further 3 hours at room temperature, the mixture is filtered, and the filtrate is basified with 5N sodium hydroxide and immediately extracted with ethyl acetate. For the extract crude 1-(N,N-dimethylamidine)-4-(4-pyridyl)-5-amino-1H-pyrazole can be isolated as a thick, dark red oil. This material can be used for synthetic purposes, but it can be purified as the hydrochloride, if necessary, 12.0 g. (61%).

To a solution of 2.3 g. of crude base dissolved in isopropanol (30 ml.) is added ethanolic hydrogen chloride solution to afford the hydrochloride salt in the form of yellow needles, 1.35 g., m.p. 206°–208°. Recrystallization of the solid from alcohol gives pure 1-(N,N-dimethylamidino)-4-(4-pyridyl)-5-amino-1H-pyrazole hydrochloride hemihydrate, m.p. 205°–206°.

Analysis calculated for $C_{11}H_{14}N_6$, HCl ½ $H_2O$ C, 47.91; H, 5.85; Cl, 12.85; N, 30.47; Found: C, 48.17; H, 5.46; Cl, 12.83; H, 30.60.

EXAMPLE 7

4-Dimethylamino-8-(4-pyridyl)-pyrazolo[1,5-a][1,3,5]-triazine

A mixture of crude 1-(N,N-dimethylamidino-4-(4-pyridyl)-5-amino pyrazole (6.9 g. 30 mmoles) and triethyl orthoformate (40 ml.) containing 4 drops of sulfuric acid is heated under reflux for 2 hours, cooled and filtered. The solid is recrystallized from ethyl acetate (ca 200 ml.) to afford 4-dimethylamino-8-(4-pyridyl)-pyrazolo[1,5-a][1,3,5]triazine (3.8 g. 54%) in the form of long, pale orange needles, m.p. 184°–185° C.

Analysis calculated for $C_{12}H_{12}N_6$ C, 59.99; H, 5.03; N, 34.98; Found: C, 59.85; H, 5.13; N, 34.72.

EXAMPLE 8

4-Methyl-4-dimethylamino-8-(4-pyridyl)-pyrazolo[1,5-a]-[1,3,5]triazine

By replacing triethyl orthoformate in Example 6 with an equal volume of triethyl ortho acetate, there is obtained 2-methyl-4-dimethylamino-8-(4-pyridyl)-pyrazolo[1,5-a][1,3,5]triazine in 51% yield in the form of pale yellow crystals, m.p. 195°–197° C. from ethyl acetate.

Analysis calculated for $C_{13}H_{14}N_6$½$H_2O$ C, 59.30; H, 5.74; N, 31.91; Found: C, 59.57; H,5.70; N, 31.74.

EXAMPLE 9

4-Pivalamido-8-(4-pyridyl)-pyrazolo[1,5-a][1,3,5]-triazine pivalic acid salt A mixture of 4-amino-8-(4-pyridyl)-pyrazolo[1,5-a][1,3,5]triazine (2.0 g., 9.4 mmoles) sodium pivalate (2.3 g.) and pivalic anhydride (30 ml.) was stirred in an oil bath at 160–170 for 3 hours, during which most of the solid went into solution and another solid precipitated. When cool, the solid was filtered off, washed with a very small amount of cold water, suspended in ethyl acetate and refiltered, 2.2 g.

Recrystallization of this solid from nitromethane gave a first crop consisting of sodium pivalate. The filtrate was evaporated and the residue recrystallized from aqueous methanol to afford 4-pivalamido-8-(4-pyridyl)-pyrazolo[1,5-a][1,3,5]triazine pivalic acid salt of m.p. 139°–141°.

Analysis calculated for $c_{15}H_{16}N_6O$. $C_4H_9COOH$ C, 60.29; H, 6.58; N, 21.09; Found: C, 60.02; H, 6.37; N, 21.41.

What is claimed is:

1. A compound having the formula:

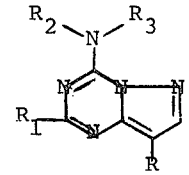

and pharmacologically acceptable acid addition salts thereof wherein R is pyridyl, pyrmidinyl or pyrazinyl; $R_1$ is hydrogen or loweralkyl; $R_2$ is hydrogen or loweralkyl; and $R_3$ is hydrogen, loweralkyl, loweralkanoyl, carbamoyl or N-loweralkylcarbamoyl.

2. The compound of claim 1 wherein R is pyridyl, pyrimidinyl or pyrazinyl; $R_1$ is hydrogen; $R_2$ is hydrogen or methyl; and $R_3$ is hydrogen, methyl, acetyl or N-ethylcarbamoyl.

3. The compound of claim 1 wherein R is pyridyl, $R_1$ is hydrogen; and $R_2$ and $R_3$ are hydrogen.

4. The compound of claim 1 which is 4-amino-8-(4-pyridyl)-pyrazolo[1,5-a][1,3,5]triazine.

5. The compound of claim 1 which is 4-amino-8-(4-pyrimidinyl)-pyrazolo-[1,5-a][1,3,5]-triazine.

6. The compound of claim 1 which is 4-amino-8-(2-pyrazinyl)-pyrazolo[1,5-a][1,3,5]triazine.

7. The compound of claim 1 which is 4-acetamido-8-(4-pyridyl)-pyrazolo[1,5-a][1,3,5]triazine.

8. The compound of claim 1 which is 4-($N^2$-ethylureido)-8-(4-pyridyl)pyrazolo-[1,5-a][1,3,5]-triazine.

9. The compound of claim 1 which is 4-dimethylamino-8-(4-pyridyl)-pyrazolo[1,5-a][1,3,5]-triazine.

10. The compound of claim 1 which is 2-methyl-4-dimethylamino-8-(4-pyridyl)pyrazolo [1,5-a]-[1,3,5]triazine.

11. The compound of claim 1 which is 4-pivalamido-8-(4-pyridyl)-pyrazolo-[1,5-a][1,3,5]-triazine.

12. A method for the reduction of bronchial constriction which comprises administering to a human afflicted with bronchial constriction an effective amount of a compound having the formula:

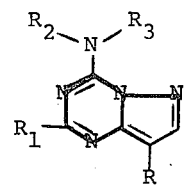

and pharmacologically acceptable acid addition salts thereof wherein R is pyridyl, pyrimidinyl or pyrazinyl; $R_1$ is hydrogen or loweralkyl; $R_2$ is hydrogen or loweralkyl; and $R_3$ is hydrogen, loweralkyl, loweralkanoyl, carbamoyl, or N-loweralkylcarbamoyl.

13. A composition useful for the treatment of bronchial constriction which comprises an inert carrier and from 5 to 100 mgs. per unit dosage a compound having the formula:
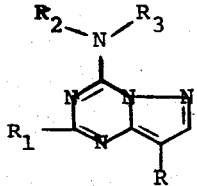
and pharmacologically acceptable acid addition salts thereof wherein R is pyridyl, pyrimidinyl or pyrazinyl; $R_1$ is hydrogen or loweralkyl; $R_2$ is hydrogen or loweralkyl; and $R_3$ is hydrogen, loweralkyl, loweralkanoyl, carbamoyl, or N-loweralkylcarbamoyl.
* * * * *